US012685458B2

(12) United States Patent
Chu et al.

(10) Patent No.: US 12,685,458 B2
(45) Date of Patent: Jul. 21, 2026

(54) PRESTRAIN ADHESIVE FOR EXTERNAL RESPIRATORY MEASUREMENT SENSORS

(71) Applicants: THE REGENTS OF THE UNIVERSITY OF CALIFORNIA, Oakland, CA (US); MAKANI SCIENCE INC., Irvine, CA (US)

(72) Inventors: Michael Chu, Irvine, CA (US); William E. Saltzstein, Irvine, CA (US); Michelle Khine, Irvine, CA (US)

(73) Assignees: THE REGENTS OF THE UNIVERSITY OF CALIFORNIA, Oakland, CA (US); MAKANI SCIENCE INC., Irvine, CA (US)

( * ) Notice: Subject to any disclaimer, the term of this patent is extended or adjusted under 35 U.S.C. 154(b) by 856 days.

(21) Appl. No.: 17/995,770

(22) PCT Filed: Apr. 9, 2021

(86) PCT No.: PCT/US2021/026629
§ 371 (c)(1),
(2) Date: Oct. 7, 2022

(87) PCT Pub. No.: WO2021/207633
PCT Pub. Date: Oct. 14, 2021

(65) Prior Publication Data
US 2023/0172482 A1     Jun. 8, 2023

Related U.S. Application Data

(60) Provisional application No. 63/007,647, filed on Apr. 9, 2020.

(51) Int. Cl.
*A61B 5/08*     (2006.01)
*A61B 5/00*     (2006.01)
(Continued)

(52) U.S. Cl.
CPC .......... *A61B 5/0816* (2013.01); *A61B 5/1135* (2013.01); *A61B 5/6832* (2013.01);
(Continued)

(58) Field of Classification Search
CPC ... A61B 5/0816; A61B 5/1135; A61B 5/6832; A61B 5/6833; A61B 5/113;
(Continued)

(56) References Cited

U.S. PATENT DOCUMENTS

| | | | |
|---|---|---|---|
| 6,882,086 B2 | 4/2005 | Kornbluh et al. | |
| 8,097,926 B2 * | 1/2012 | De Graff | H10F 39/026 |
| | | | 257/419 |

(Continued)

FOREIGN PATENT DOCUMENTS

CN     112696449 A     4/2021

OTHER PUBLICATIONS

USPTO, "Non-Final Office Action", issued in connection with U.S. Appl. No. 17/760,608, dated Feb. 25, 2025, 17 pages.
(Continued)

*Primary Examiner* — Ryan D Walsh
(74) *Attorney, Agent, or Firm* — NGUYEN TARBET IP LAW

(57) ABSTRACT

The present invention is directed to the standardization of prestrain applied to a sensor of an external respiratory measurement device. The method may comprise sandwiching the sensor between two adhesive layers and stretching the sensor by a fixed amount in order to match the length of the device to the length of a support layer. The device may then be covered by the support layer in order to keep the sensor in a state of prestrain, such that the length of the device matches the length of the support layer. The device may then be applied to the surface by the lower adhesive layer, and the support layer may then be removed, thus
(Continued)

leaving the sensor in a standardized and optimal state of prestrain.

20 Claims, 2 Drawing Sheets

(51) Int. Cl.
   *A61B 5/113*        (2006.01)
   *H10N 30/30*        (2023.01)
(52) U.S. Cl.
   CPC ......... *A61B 5/6833* (2013.01); *H10N 30/302* (2023.02); *A61B 5/113* (2013.01); *A61B 2560/0223* (2013.01); *A61B 2562/0261* (2013.01); *A61B 2562/12* (2013.01)
(58) Field of Classification Search
   CPC .... A61B 2560/0223; A61B 2562/0261; A61B 2562/12; H10N 30/302
   See application file for complete search history.

(56)                References Cited

U.S. PATENT DOCUMENTS

| | | | |
|---|---|---|---|
| 8,846,406 B1 * | 9/2014 | Martin | G01N 27/12 |
| | | | 422/82.01 |
| 10,898,138 B2 * | 1/2021 | Han | A61B 5/6833 |
| 2002/0130673 A1 | 9/2002 | Pelrine et al. | |
| 2003/0006669 A1 | 1/2003 | Pei et al. | |
| 2006/0258914 A1 | 11/2006 | Derchak et al. | |
| 2010/0096949 A1 | 4/2010 | Xu et al. | |
| 2017/0094796 A1 | 3/2017 | Lor et al. | |
| 2017/0225447 A1 | 8/2017 | Varadan et al. | |
| 2017/0258366 A1 | 9/2017 | Tupin, Jr. et al. | |
| 2018/0317845 A1 | 11/2018 | Chong Rodriguez et al. | |
| 2019/0069833 A1 | 3/2019 | Tanaka et al. | |
| 2019/0167193 A1 | 6/2019 | Palley et al. | |
| 2019/0201772 A1 | 7/2019 | Beamer | |
| 2019/0209028 A1 | 7/2019 | Baxi | |
| 2021/0055171 A1 * | 2/2021 | Harnett | G02B 6/4415 |

OTHER PUBLICATIONS

USPTO, "Final Office Action", issued in connection with U.S. Appl. No. 17/760,608, dated Jun. 17, 2025, 18 pages.
WIPO, "International Search Report and Written Opinion" issued in connection with PCT Patent Application PCT/US2020/051099, dated Dec. 15, 2020, 8 pages.
WIPO, "International Search Report and Written Opinion" issued in connection with PCT Patent Application PCT/US2021/026629, dated Sep. 27, 2021, 13 pages.

* cited by examiner

PRESTRAIN ADHESIVE FOR EXTERNAL RESPIRATORY MEASUREMENT SENSORS

CROSS-REFERENCES TO RELATED APPLICATIONS

This application claims benefit of U.S. Provisional Application No. 63/007,647 filed Apr. 9, 2020, the specification of which is incorporated herein in their entirety by reference.

BACKGROUND OF THE INVENTION

The application of external respiratory measurement sensors by an adhesive layer is an inexpensive and simple method of applying a sensor to a patient's skin and an efficient method of measuring respiratory activity by simply measuring how much the sensor is stretched as the patient's skin distends while breathing. A specialized adhesive layer is placed over the sensor such that the sensor adheres to the adhesive layer, light tension is applied to the sensor, and the sensor and adhesive layer are placed onto a patient's skin while maintaining said light tension. This method leaves open a significant amount of room for variation, however, as the amount of tension applied to the sensor may vary from doctor to doctor, thus resulting in an additional factor to consider when measuring results. Thus, there exists a present need for standardization in the prestrain applied to the sensor in the application of an external respiratory measurement sensor to a surface.

FIELD OF THE INVENTION

The present invention is directed to the standardization of prestrain applied to a sensor in the application of external respiratory measurement devices to a surface.

BRIEF SUMMARY OF THE INVENTION

It is an objective of the present invention to provide a method for standardized prestrain applied to a sensor in the application of external respiratory measurement devices. Prestrain refers to a light amount tension applied to a sensor before it is applied to a surface. Prestrain may be positive, in the case of stretching, or negative, in the case of compression.

The method may comprise two adhesive layers sandwiching a respiratory measurement sensor such that a layer of adhesive exists above and below the sensor. Pretension may then be applied to the sensor as a support layer is applied on top of the adhesive layer above the sensor such that the length of the device matches the length of the support layer while the sensor is stretched. The support layer may be a flat and stiff rectangular object with a length equal to the length of an external respiratory measurement device with the optimal amount of prestrain applied. The support layer may then be applied on top of the upper adhesive layer such that the support layer completely covers the adhesive layers and the sensor. The sensor, the adhesive layers, and the support layer may then be attached to a surface by the lower adhesive layer. The support layer may then be removed, thus leaving the sensor in a standardized and optimal state of prestrain. Without wishing to limit the invention to any theory or mechanism, it is believed that the technical feature of the present invention advantageously provides for more accurate respiratory measurements and a decrease in the room for error in adhesive sensor application. This is because variation in the manner and/or amount of prestrain applied to the sensor of the respiratory measurement device is greatly decreased by the constant amount by which the adhesive layers should be stretched, defined by the length of the support layer.

One of the unique and inventive technical features of the presently claimed invention is the prestraining of electromechanical sensors before the said electromechanical sensors are applied to the surface. Without wishing to limit the invention to any theory or mechanism, it is believed that the technical feature of the present invention advantageously provides for the resistance value of the electromechanical sensors to remain in an operational range as well as preventing the electromechanical sensor from becoming unstretched and buckling/bending. None of the presently known prior references or work has the unique inventive technical feature of the present invention. Furthermore, the feature of the presently claimed invention is counterintuitive. The reason that it is counterintuitive is because the inventive technical features of the present invention contributed to a surprising result. One skilled in the art would not prestrain the electromechanical sensors since this decreases the possible range that the sensor can stretch, and thus would not provide an accurate measurement of strain at the external location of the surface. Surprisingly, the prestrained sensor of the presently claimed invention have increased sensitivity that makes up for the decreased stretching range. Thus, the feature of the presently claimed invention is counterintuitive.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which.

DETAILED DESCRIPTION OF THE INVENTION

Figure 1:
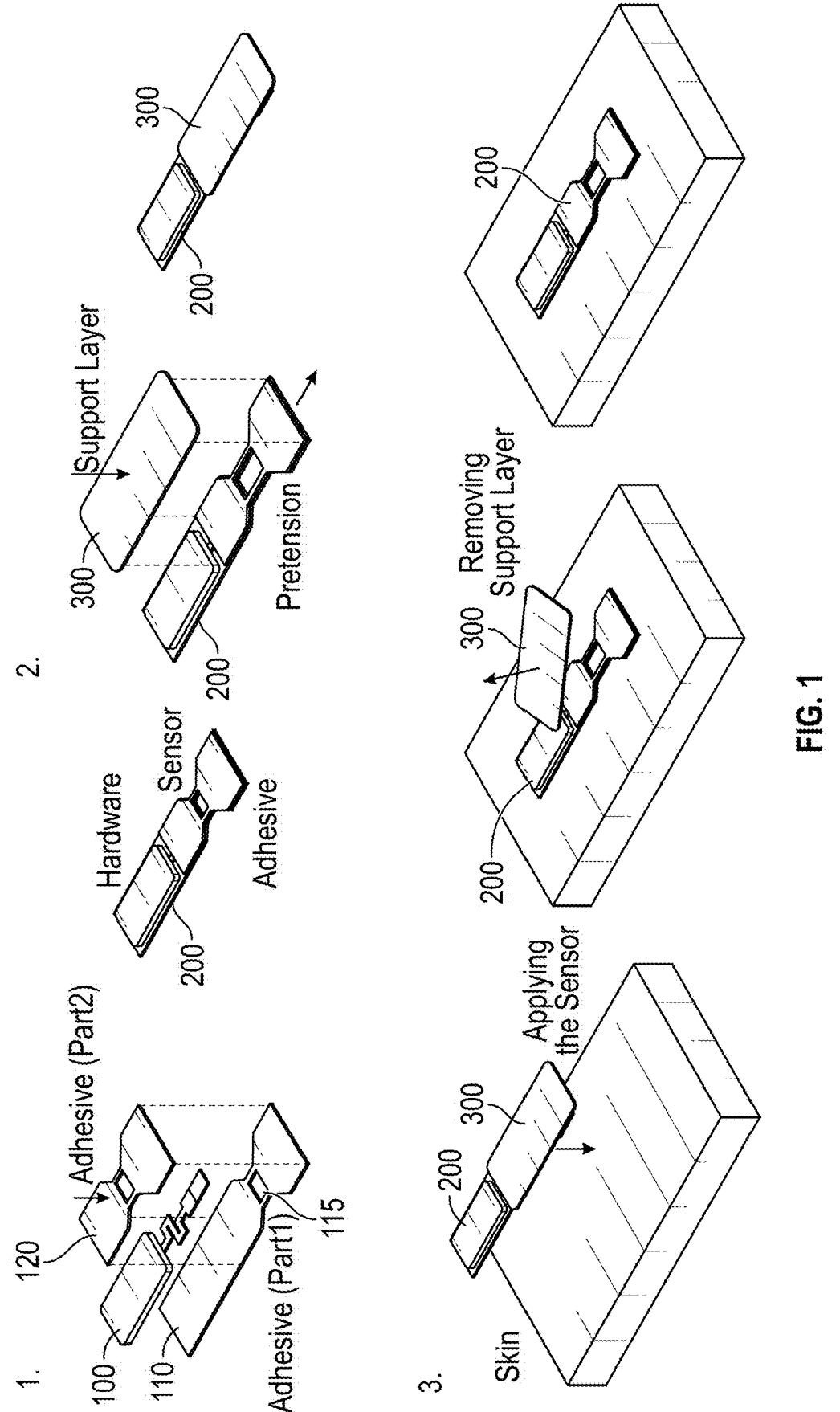
FIG. 1 shows a method for standardized adhesion of an external respiratory measurement sensor to a surface through the use of prestrain applied to a sensor before adhesion, wherein the standardized amount of prestrain is achieved by matching the length of the external respiratory measurement device to the length of a support layer.

Referring now to FIG. 1, the present invention features a method for standardized prestrain applied to a sensor of an external respiratory measurement device (ERMD). In some embodiments, the method may comprise applying a bare respiratory measurement sensor on top of a first adhesive layer. The bare respiratory measurement device may comprise a hardware device and a sensor, such that the hardware device is connected to the sensor by a wire. The sensor may be capable of stretching. The first adhesive layer may have a portion of surface area shaped to fit to the hardware device such that the hardware device may be adhered to a surface, and may have a hole slightly smaller than the size of the sensor and positioned such that at least a portion of the sensor is exposed from the bottom through the hole. The method may further comprise a second adhesive layer applied on top of the sensor such that the second adhesive layer is shaped identically to the first adhesive layer but without the portion of surface area shaped to fit to the hardware device. At this point, the sensor may be sandwiched between two adhesive layers such that the second adhesive layer completely overlaps with the first adhesive layer, making up an ERMD.

The method may further comprise applying prestrain to the sensor, such that the ERMD may match the length of a support layer. In some embodiments, prestrain is applied to the first and second adhesive layers as well as the sensor. The support layer may comprise a flat and stiff sheet of material such that the width of the support layer is equal to the maximum width of the adhesive layers and the length of the support layer is equal to the length of the ERMD when an optimal amount of prestrain is applied to the sensor. The method may further comprise applying the support layer on top of the second adhesive layer to keep the ERMD in place, such that the support layer completely covers the second adhesive layer. The ERMD with the support layer attached may then be applied to a surface by the first adhesive layer. In some embodiments, the surface may be a patient's skin. The support layer may then be removed from the device such that the sensor maintains the optimal and standardized amount of prestrain when the support layer is removed.

Figure 2:
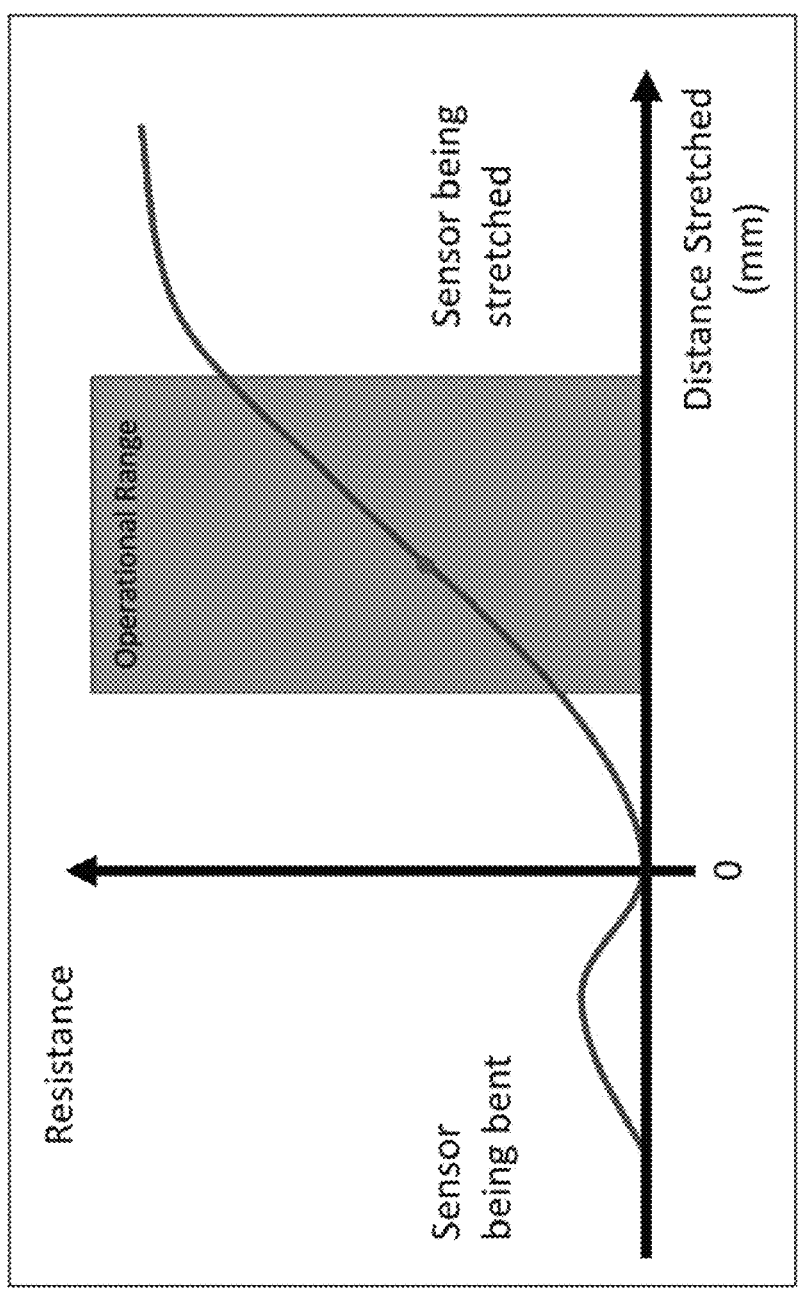
FIG. 2 shows a graph of sensor stretching distance in millimeters to resistance while highlighting the operational range that the sensor works most effectively.

The present invention features a method for applying prestrain to an electromechanical sensor (100) prior to or as the electromechanical sensor (100) is applied to an external surface of a surface. In some embodiments, the method may comprise providing the electromechanical sensor (100) comprising a sensing component, a microcontroller, and a wire communicatively coupling the sensing component to the microcontroller. In some embodiments, the electromechanical sensor (100) may be a strain sensor. In some embodiments, the electromechanical sensor (100) may be prestrained while manufacturing the electromechanical sensor (100). Prestrain may be positive, in the case of stretching, or negative, in the case of compression. The microcontroller may be capable of accepting strain reading from the sensing component and converting them into a strain signal. The method may further comprise applying the electromechanical sensor (100) to a first adhesive layer (110) comprising a first sensor aperture (115) through the first adhesive layer (110) such that at least a portion of the sensing component is exposed by the first sensor aperture (115). The exposed portion of the sensing component may allow the sensing component to more accurately measure strain at the point of application. The method may further comprise applying a second adhesive layer (120) to the sensing component to create a complete external respiratory measurement device (ERMD) (200). In some embodiments, the second adhesive layer (120) may comprise a second sensor aperture through the second adhesive layer (120) such that at least a portion of the sensing component is exposed by the second sensor aperture. The method may further comprise applying strain to the electromechanical sensor (100) such that the electromechanical sensor (100) is within an optimal sensing range based on a plurality of parameters, and holding this strain while applying a support layer (300) to the prestrained electromechanical sensor (100), wherein the support layer (300) comprises a stiff material. The plurality of parameters may comprise stretch or compression of the electromechanical sensor (100), sensitivity of the electromechanical sensor (100), upper and lower resistance boundaries of the electromechanical sensor (100), mechanical stiffness of the electromechanical sensor (100), and optimal linearity of the electromechanical sensor (100) In some embodiments, the stiff material comprises cardboard, plastic, cardstock, any other semi-rigid material, or any other rigid material. In some embodiments, the method may further comprise applying the prestrained electromechanical sensor (100) with the support layer (300) to the external surface of the surface by the first adhesive layer (110), and removing the support layer (300) such that the electromechanical sensor (100) remains in a prestrained configuration. In some embodiments, the surface may be a patient's skin. In some embodiments, the method may further comprise applying a plurality of additional electromechanical sensors (100) to the external surface of the surface. Each electromechanical sensor (100) may be disposed at a 80 to 100 degree angle to each adjacent electromechanical sensor (100), disposed 0.5 to 1.5 cm from each adjacent electromechanical sensor (100), or a combination thereof. The stretching of the sensor will shift the starting point of the resistance value (red dot in FIG. 2) to a point within the operational range of the sensor. The operational range is a window where the sensor will perform most optimally, although the sensor can also perform, though poorly, outside of the operational range. This is a way to optimize the performance of the sensor by setting the starting position to a point within the operational range. The stretching of the sensor also makes it less likely for the sensor to become unstretched and buckle. The left side of the y-axis in FIG. 2 shows what may happen then the sensor starts to buckle and bend when it isn't stretching anymore.

In some embodiments, the electromechanical sensor (100) may comprise a communication component. In some embodiments, the communication component may comprise a wire from the electromechanical sensor (100) to an external computing device. In other embodiments, the communication component may comprise a wireless transceiver/receiver communicatively coupled to an external computing device. In some embodiments, the external computing device is selected from a group comprising a microcontroller, a smart device, a medical monitor, or some other device comprising a memory component and a processor.

The present invention features a method for biasing an electromechanical sensor (100) in order to utilize a full optimal range of a signal measured by the electromechanical sensor (100). In some embodiments, the method may comprise providing the electromechanical sensor (100) and applying prestrain to the electromechanical sensor (100) based on how much the electromechanical sensor (100) is expected to contract in application, such that the electromechanical sensor (100) is within an optimal sensing range based on a plurality of parameters. The plurality of parameters may comprise stretch or compression of the electromechanical sensor (100), sensitivity of the electromechanical sensor (100), upper and lower resistance boundaries of the electromechanical sensor (100), mechanical stiffness of the electromechanical sensor (100), and optimal linearity of the electromechanical sensor (100) Prestrain may be positive, in the case of stretching, or negative, in the case of compression. Positive prestrain may be applied if the electromechanical sensor (100) is expected to compress and negative prestrain may be applied if the electromechanical sensor (100) is expected to stretch. In some embodiments, the electromechanical sensor (100) may be a strain sensor. The method may further comprise actuating the electromechanical sensor (100), such that the electromechanical sensor (100) stays within the optimal sensing range while being strained due to the prestrain applied to the electromechanical sensor (100). This can be applied to a vase variety of different applications and sensor designs.

The present invention features a method for applying prestrain to an electromechanical sensor (100) prior to or as the strain sensor (100) is applied to a surface. In some embodiments, the surface may be a patient's skin. In some embodiments, the method may comprise providing an electromechanical sensor (100). Strain may be applied to the electromechanical sensor (100) such that the electromechanical sensor (100) is within an optimal sensing range based on a plurality of parameters. In some embodiments, the plurality of parameters may comprise stretch or compression of the electromechanical sensor (100), sensitivity of the electromechanical sensor (100), upper and lower resistance boundaries of the electromechanical sensor (100), mechanical stiffness of the electromechanical sensor (100), and optimal linearity of the electromechanical sensor (100). The method may further comprise applying a double sided adhesive onto the electromechanical sensor (100). The method may further comprise applying strain to the electromechanical sensor (100) such that the electromechanical sensor (100) stretches to an optimal length through use of a tool. In some embodiments, the tool may be selected from a group comprising a ruler, a paper template, an electrical sensor such that the sensor is strained until the electrical sensor measures a specific reading, and a support layer (300) comprising a stiff material. In some embodiments, the stiff material may comprise cardboard, plastic, cardstock, any other semi-rigid material, or any other rigid material. Use of the ruler may comprise using the ruler to measure out the stretch. Use of the paper template may comprise placing the top and the bottom of a bent piece of paper, cut to the proper size, on the top and bottom of the adhesive respectively, and pulling the sensor until the piece of paper is taut. The flattened length of the piece of paper will be the final length the sensor needs to be. Use of the electrical sensor may comprise straining the sensor until a specific electrical reading and then placing the sensor. The method may further comprise applying the electromechanical sensor (100) on the external surface, and removing the tool used to measure stretch.

In some embodiments, the double sided adhesive may comprise a first sensor aperture (115) through the double sided adhesive such that at least a portion of the sensing component is exposed by the first sensor aperture (115). In some embodiments, the method may further comprise applying a plurality of additional electromechanical sensors to the external surface. In some embodiments, each electromechanical sensor may be disposed at a 80 to 100 degree angle to each adjacent electromechanical sensor. In some embodiments, each electromechanical sensor may be disposed 0.5 to 1.5 cm from each adjacent electromechanical sensor. In some embodiments, the strain may be applied to the electromechanical sensor (100) while the electromechanical sensor (100) is being manufactured. The electromechanical sensor (100) may comprise a communication component. In some embodiments, the communication component may comprise a wire from the electromechanical sensor (100) to an external computing device. In some embodiments, the communication component may comprise a wireless transceiver/receiver communicatively coupled to an external computing device. In some embodiments, the electromechanical sensor (100) may comprise a strain sensor. Positive prestrain may be applied if the electromechanical sensor (100) is expected to compress and negative prestrain may be applied if the electromechanical sensor (100) is expected to stretch.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting essentially of" or "consisting of", and as such the written description requirement for claiming one or more embodiments of the present invention using the phrase "consisting essentially of" or "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A method for applying prestrain to an electromechanical sensor (100) prior to or as the electromechanical sensor (100) is applied to an external surface, the method comprising:

a. providing the electromechanical sensor (100) wherein strain is applied to the electromechanical sensor (100) such that the electromechanical sensor (100) is within an optimal sensing range based on a plurality of parameters; and b. applying the prestrained electromechanical sensor (100) to the external surface by an adhesive layer (110); wherein an amount of prestrain is applied to the electromechanical sensor (100), wherein the amount of prestrain applied to the electromechanical sensor (100) corresponds to a predicted displacement of the external surface.

2. The method of claim 1 further comprising:

a. applying a support layer (300) to the prestrained electromechanical sensor (100), wherein the support layer (300) comprises a stiff material; and b. removing, after applying the prestrained electromechanical sensor (100), the support layer (300) such that the prestrained electromechanical sensor (100) remains in a prestrained configuration.

3. The method of claim 2, wherein the stiff material comprises cardboard, plastic, cardstock, any other semi-rigid material, or any other rigid material.

4. The method of claim 1, wherein the second adhesive layer (120) comprises a second sensor aperture through the second adhesive layer (120) such that at least a portion of the sensing component is exposed by the second sensor aperture.

5. The method of claim 1, wherein the electromechanical sensor (100) comprises a communication component.

6. The method of claim 5, wherein the communication component comprises a wire from the electromechanical sensor (100) to an external computing device.

7. The method of claim 5, wherein communication component comprises a wireless transceiver/receiver communicatively coupled to an external computing device.

8. The method of claim 1 further comprising:

a. applying the prestrained electromechanical sensor (100) to the adhesive layer (110) comprising a first sensor aperture (115) through the adhesive layer (110) such that at least a portion of the sensing component is exposed by the first sensor aperture (115);

b. applying a second adhesive layer (120) to the sensing component.

9. The method of claim 1, wherein the electromechanical sensor (100) comprises a strain sensor.

10. The method of claim 1, wherein the plurality of parameters comprises stretch or compression of the electromechanical sensor (100), sensitivity of the electromechanical sensor (100), upper and lower resistance boundaries of the electromechanical sensor (100), mechanical stiffness of the electromechanical sensor (100), and optimal linearity of the electromechanical sensor (100).

11. A method for applying prestrain to an electromechanical sensor (100) prior to or as the strain sensor (100) is applied to a surface, the method comprising:

a. providing an electromechanical sensor (100) wherein strain is applied to the electromechanical sensor (100) such that the electromechanical sensor (100) is within an optimal sensing range based on a plurality of parameters;

b. applying a double sided adhesive onto the electromechanical sensor (100);

c. applying strain to the electromechanical sensor (100) such that the electromechanical sensor (100) stretches to an optimal length through use of a tool used to measure stretch, wherein an amount of prestrain is applied to the electromechanical sensor (100), wherein the amount of prestrain applied to the electromechanical sensor (100) corresponds to a predicted displacement of the external surface;

d. applying the electromechanical sensor (100) on the external surface; and e. removing the tool used to measure stretch.

12. The method of claim 11, wherein the tool is selected from a group comprising a ruler, a paper template, an electrical sensor such that the sensor is strained until the electrical sensor measures a specific reading, and a support layer (300) comprising a stiff material.

13. The method of claim 12, wherein the stiff material comprises cardboard, plastic, cardstock, any other semi-rigid material, or any other rigid material.

14. The method of claim 11, wherein the double sided adhesive comprises a first sensor aperture (115) through the double sided adhesive such that at least a portion of the sensing component is exposed by the first sensor aperture (115).

15. The method of claim 11, wherein the electromechanical sensor (100) comprises a communication component.

16. The method of claim 11, wherein the electromechanical sensor (100) comprises a strain sensor.

17. The method of claim 11, wherein the plurality of parameters comprises stretch or compression of the electromechanical sensor (100), sensitivity of the electromechanical sensor (100), upper and lower resistance boundaries of the electromechanical sensor (100), mechanical stiffness of the electromechanical sensor (100), and optimal linearity of the electromechanical sensor (100).

18. A method for biasing an electromechanical sensor (100) in order to utilize a full optimal range of a signal measured by the electromechanical sensor (100), the method comprising:

a. providing an electromechanical sensor (100);

b. applying an amount of prestrain to the electromechanical sensor (100) corresponding to a predicted displacement of the external surface, such that the electromechanical sensor (100) is within an optimal sensing range based on a plurality of parameters; and c. actuating the electromechanical sensor (100), such that the electromechanical sensor (100) stays within the optimal sensing range while being strained due to the prestrain applied to the electromechanical sensor (100).

19. The method of claim 18, wherein the electromechanical sensor (100) comprises a strain sensor.

20. The method of claim 18, wherein the plurality of parameters comprises stretch or compression of the electromechanical sensor (100), sensitivity of the electromechanical sensor (100), upper and lower resistance boundaries of the electromechanical sensor (100), mechanical stiffness of the electromechanical sensor (100), and optimal linearity of the electromechanical sensor (100).

* * * * *